United States Patent
Gondek et al.

(10) Patent No.: US 10,614,914 B2
(45) Date of Patent: Apr. 7, 2020

(54) SECURE PATIENT DATA IN MEDICAL ENVIRONMENTS

(71) Applicant: Welch Allyn, Inc., Skaneateles Falls, NY (US)

(72) Inventors: Cory R. Gondek, Tigard, OR (US); Song Y. Chung, Canton, GA (US); Kenzi Mudge, Skaneateles, NY (US); Steven D. Baker, Beaverton, OR (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 222 days.

(21) Appl. No.: 15/796,323

(22) Filed: Oct. 27, 2017

(65) Prior Publication Data
US 2019/0130068 A1    May 2, 2019

(51) Int. Cl.
*G16H 10/60*    (2018.01)
*H04L 29/06*    (2006.01)
(Continued)

(52) U.S. Cl.
CPC ......... *G16H 10/60* (2018.01); *G06F 19/3418* (2013.01); *G06F 21/6245* (2013.01); *G16H 40/67* (2018.01); *H04L 9/0891* (2013.01); *H04L 9/0894* (2013.01); *H04L 63/0435* (2013.01); *H04L 63/0442* (2013.01); *H04L 2209/80* (2013.01); *H04L 2209/88* (2013.01)

(58) Field of Classification Search
CPC .... G16H 10/60; G16H 40/67; G06F 21/6245; G06F 19/3418; H04L 63/0442; H04L 63/0435
USPC ......................................................... 713/171
See application file for complete search history.

(56) References Cited

U.S. PATENT DOCUMENTS

| 5,737,419 A | * | 4/1998 | Ganesan | ................ | H04L 9/083 |
| | | | | | 380/286 |
| 9,129,099 B1 | * | 9/2015 | Paruchuri | ............... | G06F 21/30 |

(Continued)

FOREIGN PATENT DOCUMENTS

| WO | 2012141437 A3 | 1/2013 |
| WO | 2016151364 A1 | 9/2016 |

OTHER PUBLICATIONS

NPL Search (Year: 2019).*
(Continued)

*Primary Examiner* — Syed A Zaidi
(74) *Attorney, Agent, or Firm* — Merchant & Gould P.C.

(57) ABSTRACT

A patient care environment includes a monitoring device and a vital sign device, where the vital sign device communicates patient vital sign data to the monitoring device. A site key, entity keys, and key combining algorithms are used to secure communications in the patient care environment. Neither the site key nor the entity keys are communicated between the monitoring device and the vital sign device. The monitoring device may use the site key and entity keys to decrypt encrypted messages that have been previously stored in the vital sign device and transmitted back to any monitoring device containing the correct set of site and entity keys. The site key and entity key may also be used during the discovery and/or connection operations between the monitoring device and the vital sign device to associate a wirelessly connected vital sign device with a patient record.

19 Claims, 9 Drawing Sheets

(51) Int. Cl.
*G06F 21/62* (2013.01)
*G06F 19/00* (2018.01)
*H04L 9/08* (2006.01)
*G16H 40/67* (2018.01)

(56) References Cited

U.S. PATENT DOCUMENTS

| | | | |
|---|---|---|---|
| 9,504,388 B2 | 11/2016 | Baker et al. | |
| 2002/0010679 A1* | 1/2002 | Felsher | G06F 19/328 |
| | | | 705/51 |
| 2003/0115452 A1* | 6/2003 | Sandhu | H04L 63/045 |
| | | | 713/155 |
| 2003/0147536 A1* | 8/2003 | Andivahis | H04L 63/06 |
| | | | 380/277 |
| 2004/0193905 A1* | 9/2004 | Lirov | G06F 21/606 |
| | | | 713/193 |
| 2007/0239998 A1* | 10/2007 | Beck | G06F 21/33 |
| | | | 713/193 |
| 2008/0040602 A1* | 2/2008 | Williams | H04L 9/30 |
| | | | 713/153 |
| 2008/0287748 A1 | 11/2008 | Sapounas et al. | |
| 2009/0073991 A1 | 3/2009 | Landrum et al. | |
| 2009/0112630 A1* | 4/2009 | Collins, Jr. | G06F 19/3418 |
| | | | 705/3 |
| 2010/0030690 A1* | 2/2010 | Herlitz | G06F 21/6245 |
| | | | 705/50 |
| 2010/0324380 A1* | 12/2010 | Perkins | A61B 5/0002 |
| | | | 600/301 |
| 2011/0003610 A1 | 1/2011 | Key et al. | |
| 2011/0082798 A1* | 4/2011 | Michaud | G06Q 20/20 |
| | | | 705/71 |
| 2011/0218418 A1 | 9/2011 | Green et al. | |
| 2012/0210126 A1* | 8/2012 | Johnson | G06F 16/00 |
| | | | 713/165 |
| 2014/0197931 A1 | 7/2014 | Pless | |
| 2014/0313052 A1 | 10/2014 | Yarger et al. | |
| 2015/0009045 A1 | 1/2015 | Proud | |
| 2015/0081371 A1* | 3/2015 | Tang | G06Q 10/1095 |
| | | | 705/7.19 |
| 2015/0235065 A1 | 8/2015 | Brumer et al. | |
| 2015/0335290 A1* | 11/2015 | Hunter | A61F 2/07 |
| | | | 623/1.13 |
| 2016/0134950 A1 | 5/2016 | Sattiraju et al. | |
| 2018/0167200 A1* | 6/2018 | High | G06F 21/62 |

OTHER PUBLICATIONS

Multisense™ Strips: Clinical Quality Data in a Small, Wearable Strip, http://www.rhythmdiagnosticsystems.com/solutions/, Dec. 19, 2016, 2pgs.

Najera, Secure Architecure for the Integration of Rfid and Sensors in Personal Networks, http://link.springer.com/chapter/10.1007/978-3-642-29963-6 15#page-1, International Workshop on Security and Trust Management, Springer Berlin Heidelberg, Jun. 2011, 5pgs.

* cited by examiner

SECURE PATIENT DATA IN MEDICAL ENVIRONMENTS

INTRODUCTION

Clinicians in medical environments typically use vital sign devices to obtain and/or record one or more vital signs of patients. Some vital sign devices can display the measured parameter(s) on the device itself. Other vital sign devices transmit measured parameters to a peripheral device that displays a representation of the measured parameter. The transmission of measured parameters, which may or may not include patient identifying information, usually occurs via a wired physical layer (wired connection) between the vital sign device and peripheral device or via a wireless physical layer (wireless connection).

SUMMARY

Examples and embodiments described herein relate to systems and methods for securing communications and data, particularly between medical devices communicating patient-related data. Generally, the systems include a monitoring device, a vital sign device, and may include one or more servers for patient identification and/or electronic medical record storage. Site keys specific to a particular patient care environment, along with one or more entity keys and one or more key combining algorithms are used to secure protected health information (PHI) and other sensitive information transmitted between a monitoring device and a vital sign device and to establish trust between devices. An encrypted package containing PHI, along with other sensitive information, is known as the patient blob (binary large object).

Protected health information may be any information used to associate patient vital signs information to a specific individual including, but not limited to: Patient Identifier Numbers, Medical Record Numbers, globally unique identifiers generated by cryptographic algorithms, patient name and date of birth, device serial number, and device hardware addresses.

Site keys are digital keys that are generated at the site or facility of patient care and may change frequently. Entity keys are digital keys that are provided by other security providers vested in securing PHI. These are typically the manufacturer of the device and sometimes third party key providers, e.g. Verisign. As used herein, "entity key" means a single entity key or multiple entity keys. For instance, keys from third party key providers can be combined with existing keys.

Each entity and the patient care site do not generally have access to the other's keys to reduce the risk of a single individual having all the keys and algorithms needed to decrypt and expose sensitive patient information. Keys are never transmitted from the monitoring device. Encrypted PHI is stored in vital signs devices by the monitoring devices to allow monitoring devices with the right set of keys to connect to and read vital signs from a vital sign device and associate vital signs data with the correct patient. As used herein, the term "site key" indicates the site key and also the combination of the site key, the entity key and third party keys. In some instances, a site key does not exist and an entity key is used in place of the combination of the site key and entity key.

A part of the patient blob may be used to identify wireless vital sign devices within broadcast range of a monitoring device and may include wireless hardware addresses and information unique to each individual vital signs device that can be matched against a readable vital signs device fingerprint to trust that the data is being received from a trusted device.

In one aspect, an example method for connecting a patient monitoring device to a wireless vital signs device is disclosed. The example method can include: transmitting an encrypted patient blob to the wireless vital signs device; transmitting a patient blob request to the wireless vital signs device; receiving a patient blob communication from the wireless vital signs device; decrypting the patient blob communication using a set of keys and combining algorithms, wherein decrypting is used to determine patient identifying information; displaying the patient identifying information; receiving a request to connect to the wireless vital signs device; and forming a connection with the wireless vital signs device.

In another aspect, an example patient monitoring system includes a vital signs device and a monitoring device. The vital signs device includes a processing unit and memory. The memory stores instructions that, when executed by the processing unit, cause the vital signs device to: receive and store a patient blob; transmit a patient blob upon request; obtain vital sign data; generate a vital sign data packet containing vital sign data and optional patient blob; and transmit the vital sign data packet to a monitoring device. The monitoring device includes a monitoring device processing unit and monitoring device memory. The monitoring device memory includes instructions that, when executed by the monitoring device processing unit, cause the monitoring device to: request the patient blob; receive the patient blob; without receiving decryption keys from the vital sign device, decrypt the patient blob to determine the patient identifiers; receive the vital sign data packet from the vital signs device; display the patient identifying data and the vital sign data; and receive confirmation that the identifier corresponds to a patient.

In another aspect, an example method for monitoring vital signs of a patient in a medical environment is disclosed. The example method includes: obtaining patient and device identifying information and encrypting into a patient blob; writing the patient blob to a vital signs device; transmitting a patient blob request to the vital signs device; receiving a patient blob communication from the vital signs device; decrypting the patient blob communication using encryption keys, without receiving the keys from the vital signs device, wherein decrypting is used to determine patient identification; displaying the patient identification; receiving a request to connect to the vital signs device; forming a connection with the vital signs device; and receiving a vital sign data packet from the vital signs device.

DESCRIPTION OF THE FIGURES

The following figures, which form a part of this application, are illustrative of described technology and are not meant to limit the scope of the claims in any manner.

DETAILED DESCRIPTION

Various potential issues arise in medical environments where patient-related data are transmitted and/or stored. For instance, particularly when wireless vital sign devices are employed, measured patient data must be properly associated with the corresponding patient. Some patient rooms can include multiple patient beds, so a monitoring device in such a patient room could potentially receive wireless broadcasts from two different patients. As another example, some vital sign monitors are designed for single patient use, after which they are discarded. Bad actors can potentially access patient data stored on discarded single patient use vital sign monitors, unless the data are encrypted or otherwise disguised.

Broadly, the present disclosure is directed to securing patient data in patient care environments. In some aspects, securing patient data includes the use of a site key that is specific to a given patient care environment, and one or more entity keys that are provided and secured into the medical device by the manufacturer or other security providers such that none of the keys are known to the other entities. Keys resemble passwords, but can be hashed, encrypted, used as encryption seeds or otherwise converted into forms that are more appropriate for encryption tools. Example encryption tools include message direct algorithm 5 (MD5) and secure hash algorithm 1 (SHA-1).

In some embodiments, the site and entity keys are used in cryptographically locking vital sign and monitoring devices to operate together and with no other devices. Other devices may be assumed to be malicious or otherwise unauthorized. Relatedly, if a malicious or unauthorized device succeeds in locking a vital sign device, authorized monitoring devices will not trust vital signs data from the compromised vital sign device or associate vital sign data with a patient identifier.

Figure 1:
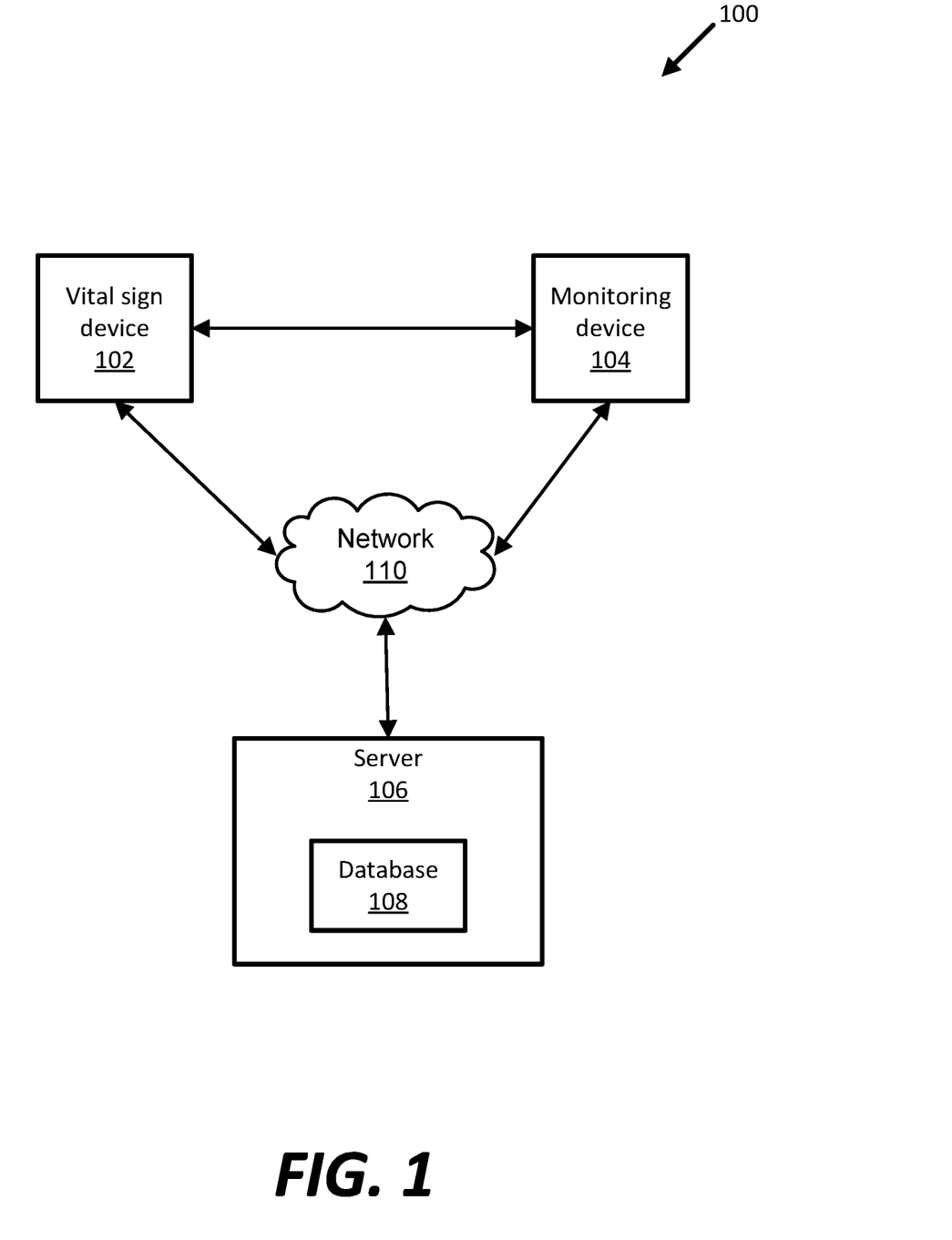
FIG. 1 shows a schematic block diagram of an example patient care environment.

FIG. 1 is a schematic block diagram of an example patient care environment 100. The example patient care environment 100 includes vital sign device 102, monitoring device 104, server 106, and database 108. Vital sign device 102 and monitoring device 104 are in communication via network 110 or other wireless technology. Monitoring device 104 and server 106 are in communication via network 110. Patient care environment 100 is typically a medical facility. Example medical facilities include clinics, hospitals, urgent care facilities, and the like. However, aspects of the instant disclosure are applicable to non-traditional medical facilities, such as temporary medical care installations, hospital-at-home, outpatient step-down facilities, and the like. Generally, components in example patient care environment 100 are used to monitor and record vital signs of a patient. Other embodiments can include more or fewer components.

Vital sign device 102 is a wireless device that is configured to obtain one or more vital sign parameters of a patient. Vital sign device 102 is not provided with the site or entity keys at any time. In the example shown, vital sign device 102 obtains vital signs data and transmits the data to a monitoring device 104. Communication of vital signs data, and other communications contemplated herein, are transmitted wirelessly between vital sign device 102 and monitoring device 104. These communications can occur over network 110 or some other out-of-band (OOB) channel. Example out-of-band channels include sound (including ultra-sonic and infra-sonic), touch, (e.g., capacitive coupling), near-field communication (NFC), Bluetooth, Bluetooth Low Energy, and infrared signals, to name a few.

The use of OOB channel can facilitate an initial connection. For example, using a touch-based capacitive coupling between the vital sign device 102 on the patient and the vital sign monitor 104 allows the communication of information such as a radio address between the vital sign device 102 and the patient monitor 104. In the case where multiple vital sign devices 102 are in range of vital sign monitor 104, the OOB transmission of the radio address allows the patient monitor 104 to determine the preferred vital sign device with which it should create an initial connection.

In an alternative embodiment, OOB transmissions can include encryption keys. Transmitting keys for encrypting data using touch provides a method of creating a secure wireless connection that mitigates man-in-the-middle attacks. These transmitted keys can include the keys to encrypt/decrypt data over the radio link and/or encrypt/decrypt a patient blob. As an example, a clinician might touch the patient and simultaneously touch the monitoring device 104 to create a touch data channel from the monitoring device 104 through the clinician and patient to the vital sign device 102.

Vital sign device 102 is capable of being removably coupled to the patient, such as through an adhesive. In some instances, vital sign device 102 is designed to be disposed of after use on a single patient. One example of such a vital sign device 102 is described in U.S. patent application Ser. No. 15/053,661 filed on Feb. 25, 2016, the entirety of which is hereby incorporated by reference. Additional details regarding vital sign device 102 are provided below with reference to FIG. 2.

Monitoring device 104 connects to, and receives communications from, vital sign device 102. The communications from vital sign device 102 can include vital sign data, encrypted PHI, and other types of data discussed below and contemplated by this disclosure. Because vital sign device 102 does not have the site key or entity key stored thereon, monitoring device 104 does not receive communications from vital sign device 102 that include the site key or entity key.

Monitoring device 104 also displays vital sign data and other data, such as patient identification. After receiving vital sign data from vital sign device 102, monitoring device 104 can transmit the vital sign data to server 106. A commercially-available example of monitoring device 104 is the Connex® Spot Monitor available from Welch Allyn® (Skaneateles Falls, N.Y.). Monitoring device 104 can be any computing device including features shown in FIG. 9, including tablets, smart-phones, lap-tops, and the like.

Monitoring device 104 includes one or more computing devices 801, shown and described below with reference to FIG. 9. In some instances, monitoring device 104 is in communication with displays viewable by one or more caregivers, such as a nursing station on a hospital floor. Also, monitoring device 104 can be in communication with caregiver-specific devices, such as hospital-issued two-way devices, pagers, mobile phones, tablet computers, etc., to deliver or communicate messages to the caregiver.

Communications between vital sign device 102 and monitoring device 104 can be subject to compromise. The potential intrusion can be attributable to the nature of wireless communications between vital sign device 102 and monitoring device 104, and/or because the example patient care environment 100 is, or can be, publicly accessible. For example, the communication between vital sign device 102 and monitoring device 104 may be disrupted by a man-in-the-middle attack. Such an attack involves the intercept of data as those data are exchanged between the vital sign device 102 and the monitoring device 104.

Additionally, in some instances, vital sign device 102 is a disposable item. Vital sign device 102 can also include or have stored thereon vital sign data. When disposable vital sign devices 102 are discarded after use, if patient identifying data (e.g., PHI) is not encrypted, or if the patient identifier can be linked to the stored data, then vital sign device 102 can be compromised by someone obtaining the discarded vital sign device 102 and accessing data stored thereon. Accordingly, the instant disclosure is directed to, at least, shielding PHI from discovery via one of the aforementioned methods or alternate methods.

Server 106 communicates with monitoring device 104 to respond to queries, receive data, and communicate with database 108. Communication from monitoring device 104 occurs via network 110, which can include requests for patient identifiers and patient vital sign data. Server 106 can act on these requests for communications from monitoring device 104, determine one or more responses to those queries, and respond back to monitoring device 104. Server 106 can access database 108 to complete transactions requested or initiated by a monitoring device 104. Server 106 includes one or more computing devices 801, shown and described below with reference to FIG. 9.

Database 108 can be one or more database systems accessible by server 106 storing different types of information. For instance, database 108 can store associations between serial numbers of vital sign devices 102 used in the patient care environment 100 and the corresponding patient identifier or patient name. Database 108 can also include electronic medical record or electronic health record data. Database 108 may reside in server 106 or on separate computing device(s) accessible by server 106.

Network 110 is typically any type of wireless network or other communication network known in the art. Examples of network 110 include the Internet, an intranet, a wide area network (WAN), a local area network (LAN), and a virtual private network (VPN), cellular network connections and connections made using protocols such as 802.11a, b, g, n and/or ac. In other examples, a wireless connection can be accomplished directly between monitoring device 104 and vital sign device 102 using one or more wired or wireless protocols, such as Bluetooth, Bluetooth Low Energy, Ant, Wi-Fi Direct, radio-frequency identification (RFID), Zigbee, and the like. When used herein, the terms "advertising," "discovery mode," and the like refer to processes for radios to notify another radio of its presence, irrespective of the physical layer and link layer. That is, the use of terms typically associated with Bluetooth technology does not limit implementation of the examples disclosed and contemplated herein to only Bluetooth radios.

Figure 2:
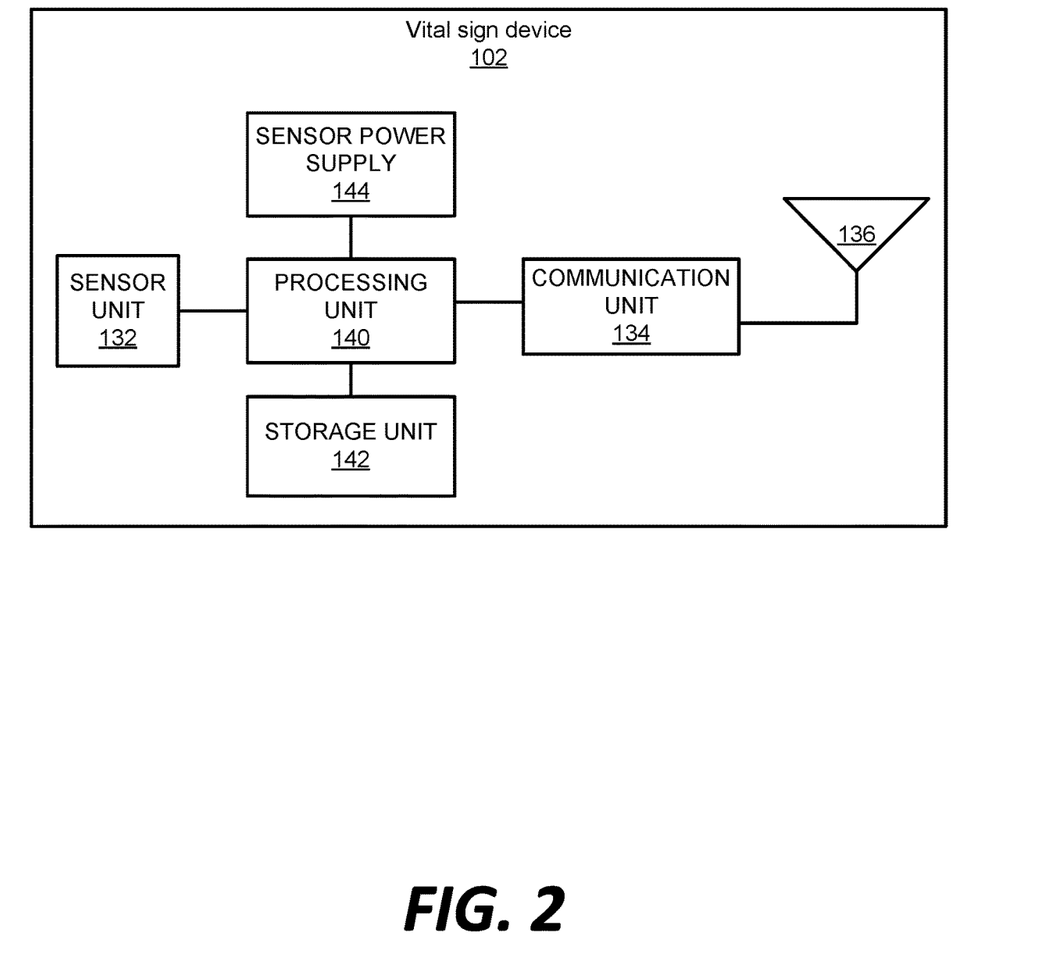
FIG. 2 shows a schematic block diagram of components of a vital sign device used in the patient care environment of FIG. 1.

FIG. 2 schematically illustrates an example of vital sign device 102, used to measure physiological parameters of the patient. In the example shown, the vital sign device 102 includes a sensor unit 132, a communication unit 134, antenna 136, a processing unit 140, a storage unit 142, and sensor power supply 144. In other embodiments, the vital sign device 102 can include one or more components in addition to the components described above, and/or replace one or more of the components described above by different components. In some examples, the vital sign device 102 is at least partially implemented in an integrated circuit.

The sensor unit 132 includes one or more sensors operable to detect one or more physiological parameters. In some embodiments, each sensor is configured as a sensing sub-circuit in a circuit board of the vital sign device 102.

In some examples, the sensor unit 132 includes one sensor for detecting one type of physiological parameters. In other examples, the sensor unit 132 includes a plurality of sensors for detecting the same or different types of physiological parameters. Example sensors of the sensor unit 132 include temperature sensors, heart rate sensors, electrocardiogram (ECG) sensors, respiratory rate sensors, accelerometers, SpO2 sensors, heartrate variability sensors, galvanic skin response sensors, blood pressure sensors, blood glucose sensors, blood oxygen sensors, and any other sensors suitable for measuring physiological parameters. The sensor unit 132 can further include one or more sensors (e.g., accelerometer) for detecting the subject's activity and posture, such as whether the subject is standing, sitting, laying down, or engaged in physical activity, such as running. In some examples, the sensor unit 132 is powered by the sensor power supply 144.

The communication unit 134 operates to communicate with the monitoring device 104. The communication unit 134 can receive signals from the monitoring device 104 via the wireless communication link and transmit data (e.g., vital sign data) to the monitoring device 104. For example, the communication unit 134 can operate as a transponder configured to emit an identifying signal in response to an interrogating received signal from the monitoring device 104. The communication unit 134 is configured as an interface suitable for communicating with the monitoring device 104, such as near field communication (NFC), radio frequency identification (RFID), Bluetooth, Wi-Fi, and other short-range wireless communications. In other examples, the communication unit 134 is further configured to communicate with monitoring device 104 and/or other computing devices via network 110.

Antenna 136 is configured to receive and transmit short range communications, such as radio frequency (RF) signals, infrared signals, and the like. In some examples, the antenna 136 is made flat so as to be incorporated into the vital sign device 102. Other configurations are also possible in other embodiments.

The processing unit 140 operates to control the sensor unit 132 and other components in the vital sign device 102. An example of the processing unit 140 includes a central processing unit (CPU). Further, the processing unit 140 operates to communicate with the monitoring device 104. In some examples, the processing unit 140 receives signals from the antenna 136. In some examples, a demodulator is provided to demodulate an RF signal received via the antenna 136. The demodulator can be implemented in a way known in the art, including, for example, attenuator stage and amplifier stage.

The processing unit 140 can perform various operations and generate an output signal for transmission. In some examples, a modulator is provided to modulate an output signal generated by the processing unit 140. The modulated signal is transmitted through the antenna 136 to the monitoring device 104. The modulator can be implemented in a way known in the art, including, for example, driver stage and amplifier stage. The processing unit 140 can be implemented in a way known in the art, including, for example, a processor, a decoder, and an encoder.

The storage unit 142 includes one or more memories configured to store vital sign data and/or applications executed by processing unit 140. As described herein, vital sign data can include physiological parameter data (e.g., measurement data) obtained from the sensor unit 132 and other data associated with the vital sign device 102 and/or the patient. At least a portion of the vital sign data is transmitted to and readable by monitoring device 104. The storage unit 142 can be of various types, including volatile and nonvolatile, removable and non-removable, and/or persistent media. In some embodiments, the storage unit 142 is an erasable programmable read only memory (EPROM).

The sensor power supply 144 is included in the vital sign device 102 and provides power to operate the sensor unit 132 and associated elements, such as the processing unit 140 and the storage unit 142. In some examples, the sensor power supply 144 includes one or more batteries, which is either for single use or rechargeable.

Figure 3:
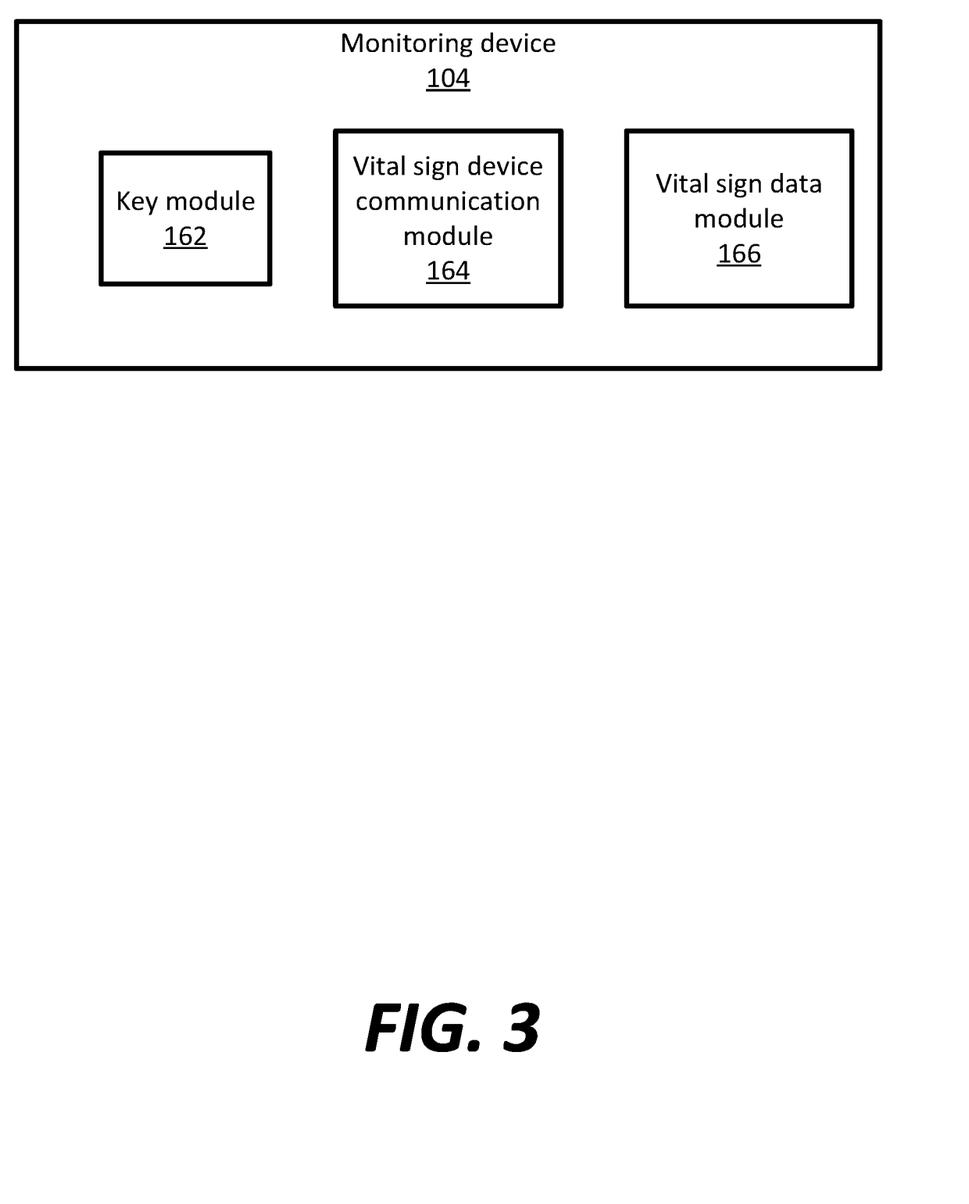
FIG. 3 shows a schematic block diagram of logical components of a monitoring device used in the patient care environment of FIG. 1.

FIG. 3 is a schematic illustration of example computing modules for monitoring device 104. As shown, example computing modules include key module 162, vital sign device communication module 164, and vital sign data module 166. Typically, example modules 162, 164, 166 are stored in memory 803, such as mass storage device 814 shown in, and described with reference to, FIG. 9. Monitoring device 104 includes other modules, not shown in FIG. 3, that are responsible for various other operating functions of monitoring device 104.

Key module 162 manages receipt, storage, and usage of site and entity keys. When necessary for encryption or decryption of the patient blob, monitoring device 104 is provided with site and entity keys. Monitoring device 104 is configured such that it never transmits or shares the site or entity keys, in full, with any other device. Key module 162 is also responsible for making the keys inaccessible outside of the monitoring device 104.

Each monitoring device 104 at a given patient care facility may use the same site key. Alternatively, different site keys may be used in different departments determined by facility security policy and needs. In some instances, the site key is changed for any of a number of reasons, such as expiration, device compromise, and/or stolen devices, to name a few. When provided with a new or replacement site key, key module 162 may retain the previous site key for a predetermined amount of time to enable communication with vital sign device 102 still storing patient health data encrypted with an old site key.

Examples below are provided solely for illustration, to exemplify how site keys can prevent or allow monitoring devices from decrypting PHI data in the blob from a vital sign device 102. As one example, a department is arranged such that all monitoring devices have the same site keys. As used herein, "department" includes different areas of a healthcare delivery organization and a second department may be a care area that is part of a different healthcare delivery organization. In this implementation, any monitoring device 104 can decode a patient blob from any vital sign device 102 that was provisioned in that department.

In another embodiment, different departments use different site keys. In this implementation, monitoring devices 104 from a first department would not be able to decode a patient blob from a vital sign device 102 provisioned in a second department.

Building on that alternative implementation, when a patient is transferred from a first department to a second department, public-private key encryption may be used. In this case, monitoring device 104 in the first department connects to the vital sign device 102 on the to-be-transferred patient and a user selects an option displayed on monitoring device 104 to transfer the patient. The first-department monitoring device 104, which can decode the patient blob, does so and then encrypts the patient blob with the public key from the second department. The first-department monitoring device 104 also sends the public-key-encrypted data to a server, another monitoring device 104 in the second department, or other storage/transmission means such as a memory stick. The second department's monitoring device 104 decrypts the patient blob using its private key. When the patient and vital sign device 102 arrive in the second department, the second department's monitoring device 104 connects to vital sign device 102. The second department's monitoring device 104 also confirms that it is the correct device to ensure that the unique IDs of the vital sign device 102 match the unique IDs (e.g., radio address, serial number) in the patient blob. Assuming the IDs match, then the monitoring device 104 displays the PHI read from the decrypted blob, allowing the clinician to confirm that this is the correct patient. The monitoring device 104 then encrypts the patient blob using its site key and transmits the encrypted blob to the vital sign device 102. The clinician's confirmation that this is the correct patient constitutes a request to connect to the vital sign device.

Vital sign device communication module 164 manages discovery of, authenticated connection to, and communication with, vital sign device 102. As discussed in greater detail below, monitoring device 104 can generate an encrypted patient blob and write the patient blob to a locked (trusted) vital sign device 102. Discovery, connection, and communication with vital sign device 102 are discussed in greater detail below with reference to, at least, FIGS. 4-9.

Connections between vital sign device 102 and monitoring device 104 consist of at least two phases. The first phase is the connection of the physical layer and may include the link layer. This allows the connected devices to share initial information for purposes such as authentication. This may be referred to as a first connection, an initial connection, or simply as a connection. An example is a Wi-Fi network where a client connects to an access point and is only allowed to transmit and receive Extensible authentication protocol packets to the authentication server. Other requests, such as DHCP, are ignored and discarded by the authenticator until the authentication is successful. Once authentication is complete, the client is allowed network access. The access level may be a function of the features embedded within the 802.1x certificate. In this disclosure, authentication is made by successful decryption of the patient blob, providing access to the protected data. Successful decryption may include the clinician confirming that the patient identifying data are correct. Correct may include that the data are intelligible and/or that displayed patient identifying data are correct for the instant patient. The second phase occurs after an initial connection and after successful decryption of the patient blob: the system has an authenticated connection. In some places, connection may mean an authenticated connection.

Generally, the patient blob includes one or more identifiers that can be used to identify a patient whose vital signs are being measured. The monitoring device 104 encrypts the patient blob using the site and entity keys stored on monitoring device 104. Notably, vital sign device 102 does not have the keys required to understand or decrypt the patient blob. However, vital sign device 102 can provide the patient blob upon request, including during connection and discovery phases. Additionally, although it is accessible, the encrypted patient blob is indistinguishable from random numbers except for monitoring devices 104 having the site key and all applicable entity keys.

In some embodiments, vital sign devices 102 may be locked to a set of monitoring devices 104 containing a unique set of site and entity keys by including a vital sign device fingerprint within the patient blob. The fingerprint can include any publicly discoverable digital information about the vital sign device that is combined, encrypted, and written back to the vital sign device. Example publicly discoverable digital information includes radio address, IMEI number, CPU serial number, manufacturer programmed serial number, or any other data that provide differentiation among vital sign devices and between vital sign devices and other wireless devices. The vital sign device 102, not having the keys to decrypt and read the data in the patient blob, would have difficulty in spoofing the contained values back to the monitoring device 104. The monitoring device 104, comparing values in the patient blob against the publicly discoverable data from the vital sign patch, would have confidence that the data have not been copied and transmitted by a man-in-the-middle or a spoofing device.

Vital sign data module 166 manages receipt and transmission of data related to the patient. For example, vital sign data module 166 receives an encrypted patient blob from vital signs device 102 and uses the site key and entity key to decrypt the patient blob. Vital sign data module 166 can then transmit vital sign data and patient identifying data to server 106. Other possible actions performed by any of modules 162, 164, 166 are discussed in greater detail below.

Figure 4:
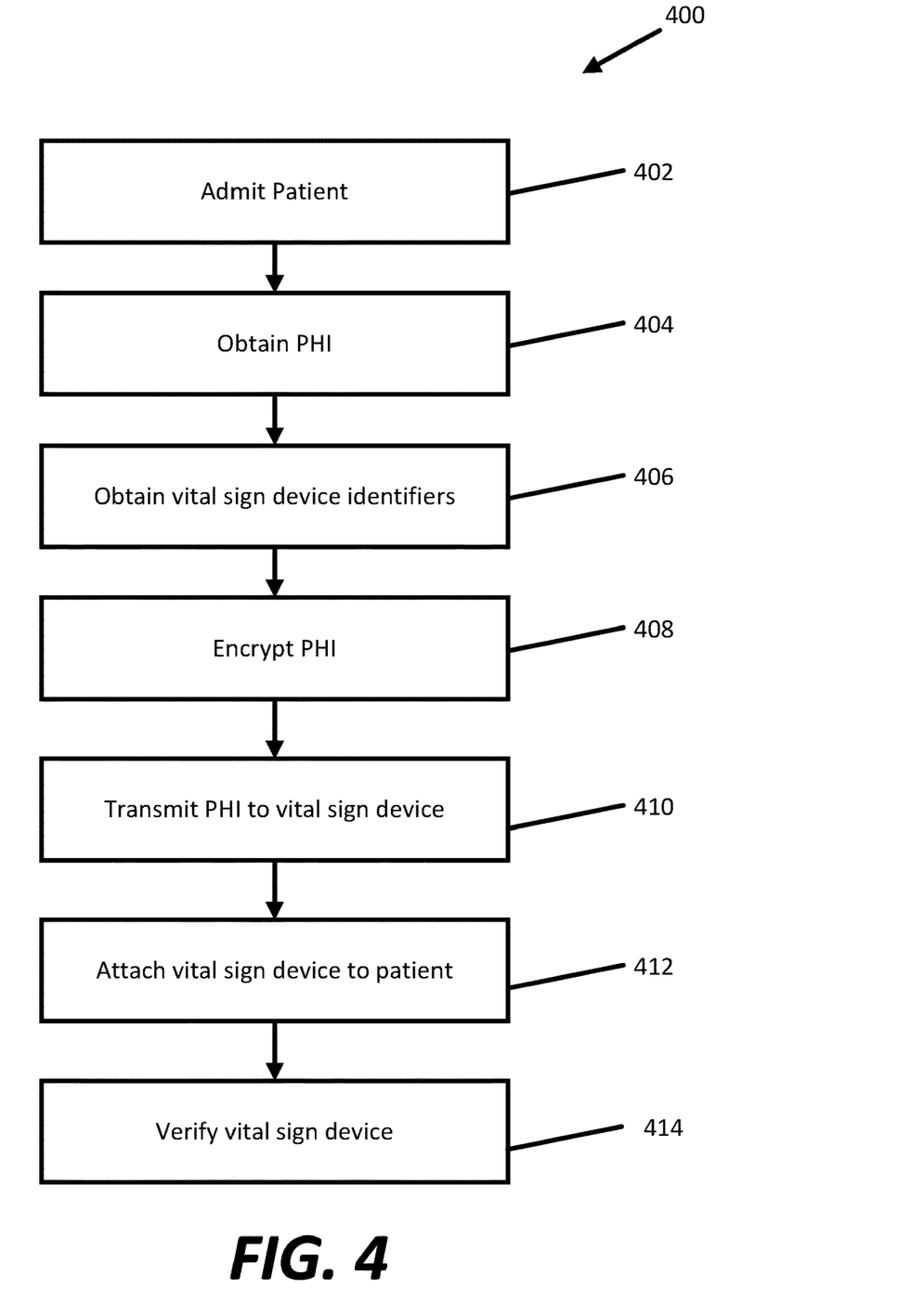
FIG. 4 shows an example method for provisioning a vital signs monitor.

FIG. 4 is an example method 400 for provisioning a vital signs monitor. The example method 400 includes admitting a patient (operation 402), obtaining PHI (operation 404), obtaining vital sign device identifiers (operation 406), encrypting the PHI (operation 408), transmitting the PHI to the vital sign device (operation 410) whereupon the vital sign device stores the encrypted PHI, attaching the vital sign device to the patient (operation 412), and verifying the vital sign device operation (operation 414). Other embodiments can include more or fewer operations. Obtaining PHI may also be referred to as obtaining an identifier.

Example method 400 begins when a patient is admitted (operation 402). Admitting a patient (operation 402), can include entering patient data into a database, such as an electronic health record database, and/or obtaining other patient identifying data, such as birthdate, social security number, first-middle-last name, and the like.

Next, patient identifying information (at least one patient identifier) is obtained for the patient (operation 404). The patient identifying information is to be securely transmitted to, and securely stored on, the vital sign device. Obtaining patient identifying information can include selection of the patient from a patient list from a server, scanning the patient wristband, manually entering patient data into the monitoring device through a keypad or touchscreen, or any number of methods for entering data into an electronic device. The patient identifier may be a globally unique identifier used as a database key. Optionally, vital sign device identifiers are read from the vital sign device (operation 406).

The patient identifying data are encrypted (operation 408) using the site key and entity key. Optionally, other data such as vital sign device identifiers can also be encrypted during operation 408. The site and entity keys are combined using a number of combining algorithms to produce an encryption key which is then used in a cryptographic algorithm, such as AES-256, to produce a patient blob. The patient blob may be further obscured by prepending random data to the patient identifying data before encrypting to ensure that the exact same data encrypted twice does not produce the exact same sequence of numbers.

The encrypted patient blob is then transmitted to the vital sign device (operation 410) to be stored by the vital sign device in non-volatile memory.

Next, the vital sign monitor is attached to the patient (operation 412). This operation is typically performed by the clinician.

Then, vital sign device operation is verified for correctness (operation 414). Verifying the correctness of vital sign device provisioning (operation 414) can include verifying that communication between the vital sign monitor and the monitoring device is functioning and enabled. Operation 414 can also include verifying that a monitoring device is receiving data from a patient and that a decoded blob has the patient's correct identifying information. Various methods for verifying that the vital sign device is provisioned correctly are described in more detail below.

Figure 5A:
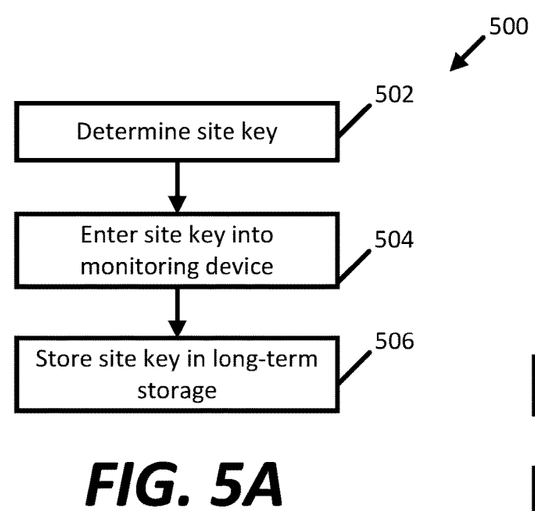
FIG. 5A shows an example method for an initial installation of a site key and a monitoring device.

FIG. 5A is an example method 500 for an initial installation of a site key and a monitoring device. After the site key is entered into each monitoring device, the site key is inaccessible outside of the monitoring device. The site key may be stored in a cryptomemory such as the Atmel AT88SC0104CA to further encrypt the key and prevent discovery even if bad actors/elements have physical access to the device.

Example method 500 begins by determining a site key (operation 502). The site key can be of varying length, may be a word in a given language, and/or may be encrypted or hashed. Typically, a site key is chosen by a person or entity installing the monitoring device at the medical facility.

Then, the site key is entered into the patient monitoring device (operation 504). Entering the site key into the patient monitoring device (operation 504) can be done via wired or wireless connection, such as an out-of-band channel or Bluetooth, manually entered via key or touchpad, scanned in using a hand scanner or camera, or any number of ways to enter data. Last, the site key is stored securely in long-term storage (operation 506).

Figure 5B:
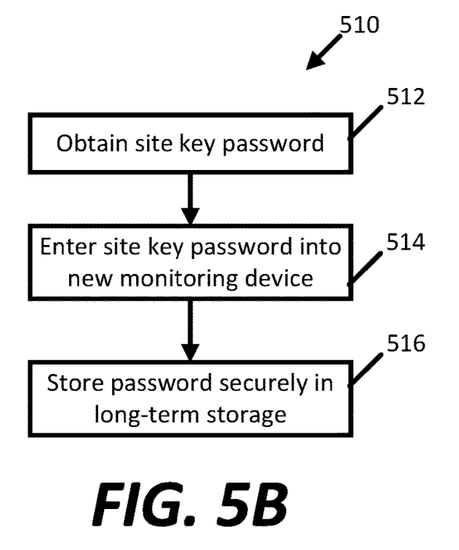
FIG. 5B shows an example method for commissioning a new patient monitoring device.

FIG. 5B is an example method 510 for commissioning a new patient monitoring device. In example method 510, other patient monitoring devices have already been commissioned and installed in the medical facility and operating for a given amount of time. Example method 510 may be employed, for example, when a particular monitoring device ceases working, is broken, or additional monitoring devices are needed at the medical facility.

Example method 510 begins by obtaining the site key (operation 512), this is usually created by and known to a site system administrator. After obtaining the site key (operation 512), the site key is entered into the new patient monitoring device (operation 514). Methods for entering the site key (operation 514) are discussed above, at least, with respect to operation 504. Last, the site key is stored securely in long-term storage (operation 516).

Figure 5C:
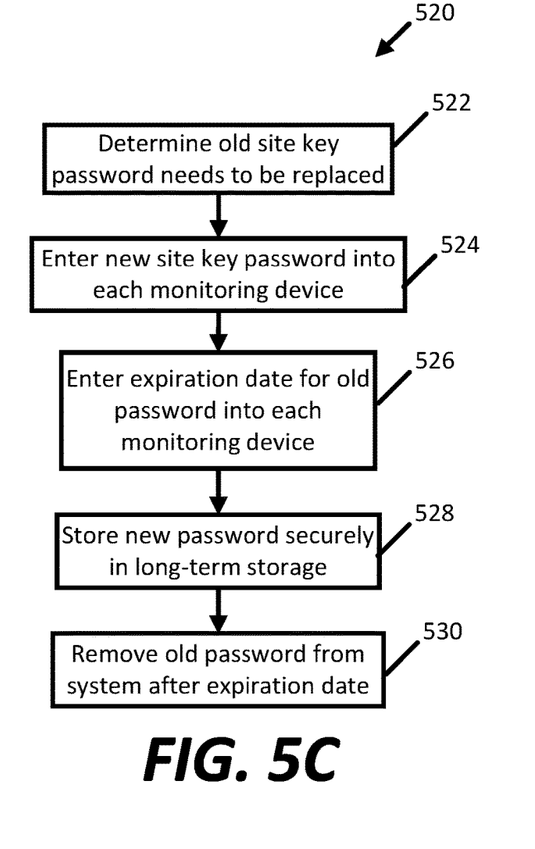
FIG. 5C shows an example method for replacing a site key at a given patient care environment.

FIG. 5C is an example method 520 for replacing a site key at a given patient care environment. The site key may need to be replaced at a given patient care environment because of concerns about security breaches, stolen devices, and/or as part of a periodic site key update policy. When replacing the site key, a user installing the site key into the patient monitoring devices has, in some embodiments, the option to make old site keys expire in the future, such as after a week. In this way, existing monitoring devices may continue to communicate with vital sign devices having expired site keys for a limited amount of time.

Example method 520 begins with a determination that the old site key needs to be replaced (operation 522). As mentioned above, this determination (operation 522) can be triggered automatically by password update policies, by security breaches, and/or other concerns. Next, a new site key is entered into each monitoring device (operation 524). The user installing the password or an entity associated with installation user determines the new site key. Example methods for entering the new site key into each monitoring device are described above with reference to operation 504.

Optionally, example method 520 may include entering an expiration date for the old password into each monitoring device (operation 526). Because some vital signs devices may still be using the old site key, optional operation 526 enables those vital signs devices with the old password to continue communicating with patient monitoring devices having the new site key for a predetermined about of time. The expiration date can be a particular date, time, or an amount of time, such as one week.

Then the new password is stored securely in long-term storage (operation 528). Last, after the expiration date, the old password is removed from the system (operation 530).

Figure 6:
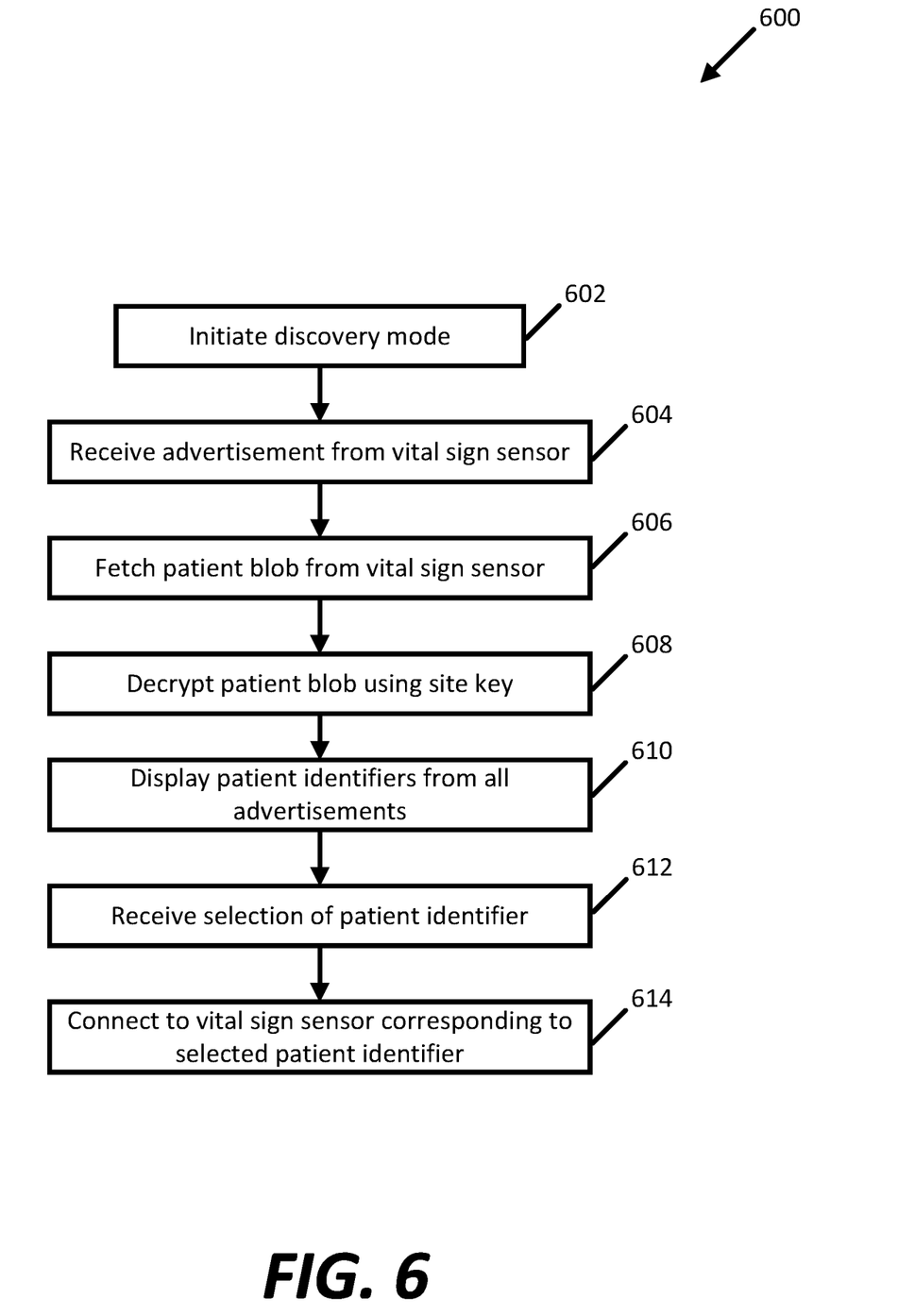
FIG. 6 shows an example method for connecting to a vital sign device.

FIG. 6 is an example method 600 for connecting to a vital sign device. The example method 600 includes initiating discovery mode (operation 602), receiving an advertisement (operation 604), fetching patient blob (operation 606), decrypting patient blob (operation 608), displaying patient identifiers (operation 610), receiving a selection of patient identifier (operation 612), and connecting to a vital sign device (operation 614). Other embodiments include more or fewer operations.

Typically, before example method 600 is performed, a vital sign device has been locked to the site key. Vital signs devices can be locked to the site key in various ways. As one example, symmetric locking may be used, where an access password was previously given to the vital sign device and shared with the monitoring device. In symmetric locking, a symmetric encryption is used to hide the vital sign device's access password in a way that can only be revealed with the site key. Then, the vital sign device can provide the encrypted password to the monitoring device, which can decrypt the password using the site key.

Asymmetric locking is another option. Asymmetric encryption is used to equip the vital sign device to send encrypted messages to the monitoring device. In one embodiment, the vital sign device is provided with a public key. As mentioned above, the site keys are kept only on the patient monitoring devices and never revealed. To validate that the monitoring device has the site key, the vital sign device can query the monitoring device to sign a random message requiring the site key, and the vital sign device will validate the signature using the public key.

Example method 600 begins by initiating a discovery mode (operation 602). In most instances, connection between a patient monitoring device and a vital sign device is performed using a Bluetooth protocol, such as Bluetooth Low Energy. In those instances, a discovery mode is initiated for the patient monitoring device. Generally, the discovery mode enables the patient monitoring device to learn what devices are available for connection. For BLE devices, when in discovery mode, the patient monitoring device can receive broadcast advertisements from other Bluetooth-enabled devices within a RF range. For one or more of these in-range devices, the monitoring device may create an initial connection, which allows it to request other information, such as the patient blob.

Upon initiating discovery mode (operation 602), the patient monitoring device receives advertisements from one or more vital sign devices (operation 604). In fact, the patient monitoring device can receive advertisements from other non-vital sign devices within a range if those devices are broadcasting advertisements via Bluetooth. For purposes of this disclosure, however, the focus will be on connecting to a vital sign device. As mentioned above, there may be more than one vital sign devices within broadcast range of a particular patient monitoring device. Therefore, a patient monitoring device may receive advertisements from more than one vital signs devices, for example, when multiple patients are within the same room of a medical facility.

After receiving an advertisement (operation 604), patient monitoring device then fetches a patient's blob from the vital sign device advertising (operation 606). Operation 606 typically includes a transmitted message including a request for the patient blob. However, other methods of fetching a patient blob from vital sign devices are possible. As mentioned above, the vital sign device does not have the site key or entity key so the vital sign device cannot decrypt the patient blob and therefore cannot identify the particular patient.

After receiving the patient blob from the vital sign device (operation 606), the patient monitoring device decrypts the patient blob using a decryption key (operation 608). Here, the patient monitoring device decrypts the encrypted patient blob received from the vital sign device by generating a decryption key using the site key and entity key. In some instances, the patient blob might have been encrypted using an out of date or expired site key. In those instances, the patient monitoring device can access the database having one or more stored, but expired, passwords to decrypt the patient blob.

After a pre-determined amount of time, after which a patient monitoring device has received one or more advertisements by nearby vital sign devices, the patient monitoring device displays the patient identifiers from all advertisements (operation 610). In operation 608, discussed above, upon decrypting the patient blob, the patient monitoring device either receives a patient identifier (PID) or a globally-unique identifier (GUID). Where the patient monitoring device receives the PID, the identifier is displayed by the patient monitoring device during operation 610.

Alternatively, when a GUID is used, the patient monitoring device transmits a query to a server and/or a database requesting an identifier corresponding to the GUID. Accordingly, the identifiers retrieved from the database are displayed during operation 610. Typically, the patient identifiers displayed during operation 610 enable a clinician to view all vital sign devices within range of the patient monitoring device and select the proper vital sign device accordingly.

After displaying the patient identifiers (operation 610), the patient monitoring device receives a selection of one of those patient identifiers (operation 612). The selection of a particular patient identifier may be received via touch (such as when a patient monitoring device has a touch sensitive screen), and/or by input methods, such as a keyboard, mouse, and the like.

After receiving a selection of a patient identifier (operation 612), which corresponds to the patient of interest, the patient monitoring device connects to the vital sign device corresponding to the selected patient identifier (operation 614). As mentioned above, connection between the patient monitoring device and vital sign device can occur via various wireless protocols, such as Bluetooth and Bluetooth Low Energy.

Figure 7:
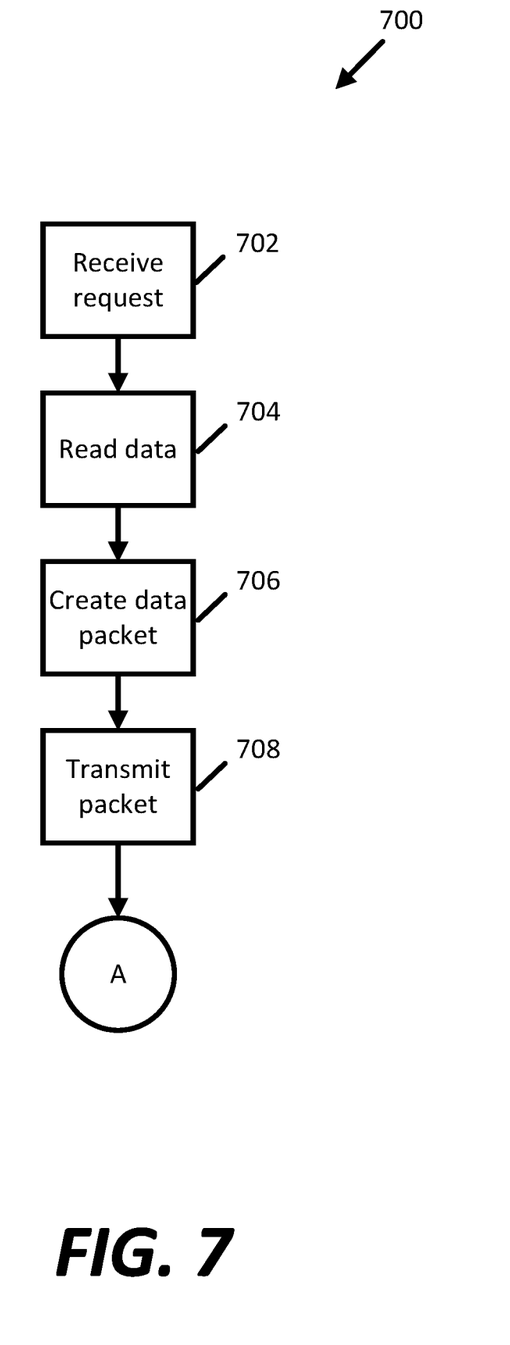
FIG. 7 shows an example method for reading and transmitting vital signs data.
Figure 8:
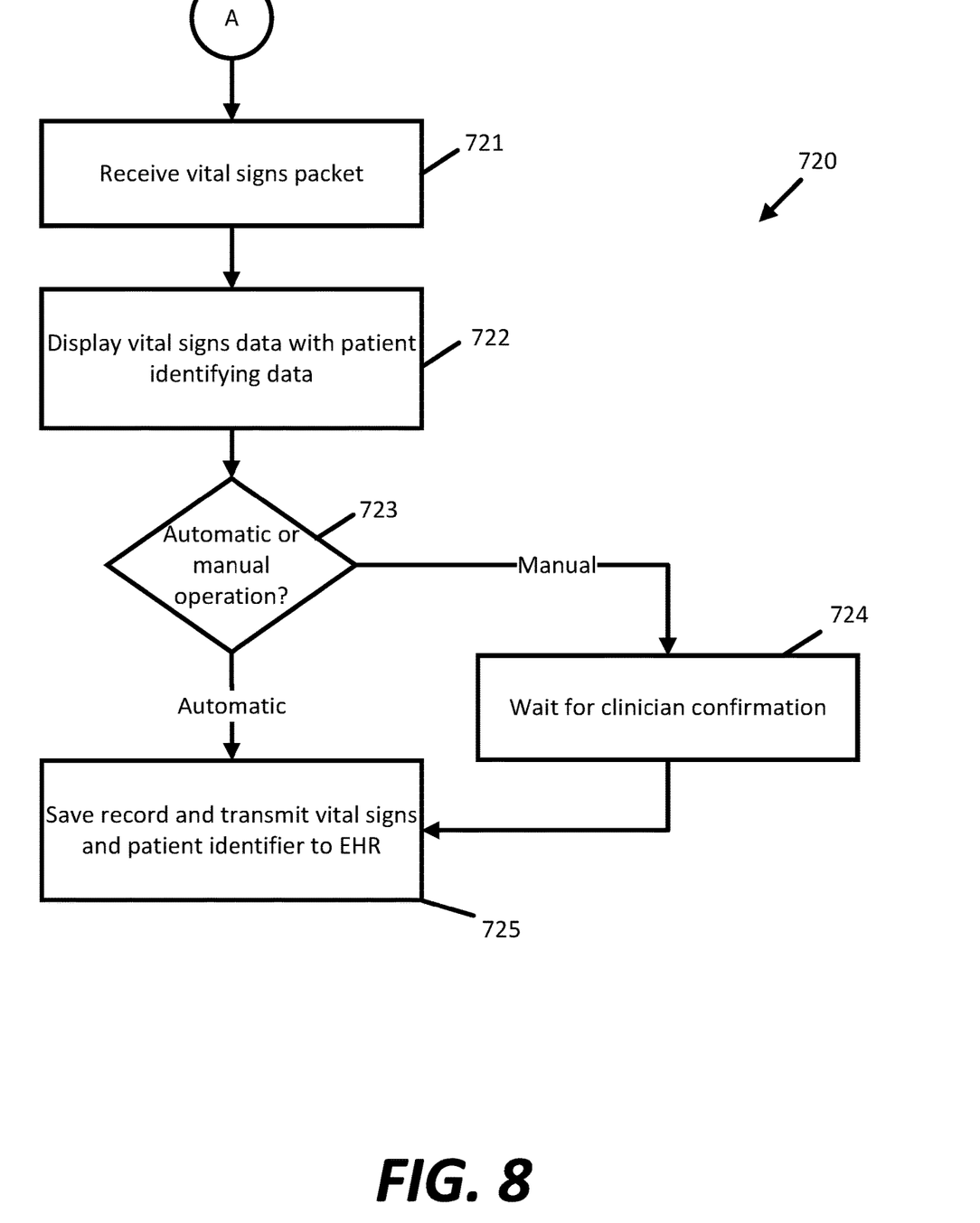
FIG. 8 shows an example method for receiving, analyzing, and transmitting vital signs data.

FIG. 7 is an example method 700 for reading and transmitting vital signs data, typically from a vital signs device to a patient monitoring device. FIG. 8 shows an example method 720 that continues from example method 700 shown in FIG. 7. Example method 720 in FIG. 8 is typically performed by a patient monitoring device. FIGS. 7 and 8 are discussed concurrently below. Other embodiments can include more or fewer operations.

Prior to execution of example method 700, the vital sign device has been provisioned, the vital sign device has been locked to a patient and set of encryption keys with the patient blob, the vital sign device has been selected as a device to provide patient vital sign data, and the vital sign device is connected to a patient monitoring device.

Example method 700 begins by receiving a request (operation 702). Usually the request is received by a vital sign device from a monitoring device requesting one or more types of data. The request can simply be a request for vital signs data, for instance. A request can be initiated, for example, by a clinician at a patient monitoring device, at selected intervals via the patient monitoring device, and/or by proximity of a clinician to the patient monitoring device.

After receiving the request (operation 702), the vital signs monitor reads one or more vital signs data (operation 704). The vital signs data read from one or more vital sign sensors on the vital sign device may be acquired at that moment or at an earlier time and stored in memory. In the latter instance, the read data operation 704 reads from memory instead of directly from sensors.

Once the vital sign data has been acquired directly from sensors or storage, a vital signs packet is constructed (operation 706). Depending on the communication protocol selected, creating a vital signs packet (operation 706) will usually include extra information to ensure the packet is sent to the monitoring device that requested the data. The vital signs packet may also include encryption and error correction as defined by the communications protocol.

The vital sign data communications packets is then transmitted (operation 708) to the requestor.

Continuing on FIG. 8, vital sign packet is received by the monitoring device (operation 721). Then the monitoring device displays vital signs data along with the associated patient identification previously received (operation 722). In some instances, data display may be continuous to reflect ongoing measurements obtained by the vital signs device.

Next, the monitoring device receives selection of manual or automatic vital signs collection (operation 723). If the configuration is manual collection, the monitoring device will wait for clinician confirmation (operation 724) before continuing. Waiting for clinician confirmation (operation 724) can be done in a variety of ways, including providing a prompt for a clinician to confirm that the data corresponds to the patient, using a database service to lookup patient name and data of birth using a database key, and/or to provide a vital sign device identification number.

If the monitoring device is configured to operate in an automatic collection mode, the monitoring device may continue collecting vital sign data without waiting for confirmation. Often, the monitoring device will be configured to wait for a clinician to visually evaluate the vital signs data and patient identification for correctness before storing the information in a persistent patient record such as an electronic medical record, electronic health record, or hard copy.

After confirming that the vital signs data are correct and correspond with the identified patient, or through an automatic operation, the patient record including the vital signs and patient identification is saved to persistent storage on the monitoring device and/or sent to a networked electronic health record system (operation 725). Storage of data in the patient record may be done automatically by the monitoring device. Alternatively, data storage in the patient record may be accomplished through a step of a user reading data from the monitoring device and transcribing the data into an electronic health record terminal.

As discussed above, one or more databases may be accessible by the server such that it can query and retrieve patient identification corresponding to the patient of concern.

Figure 9:
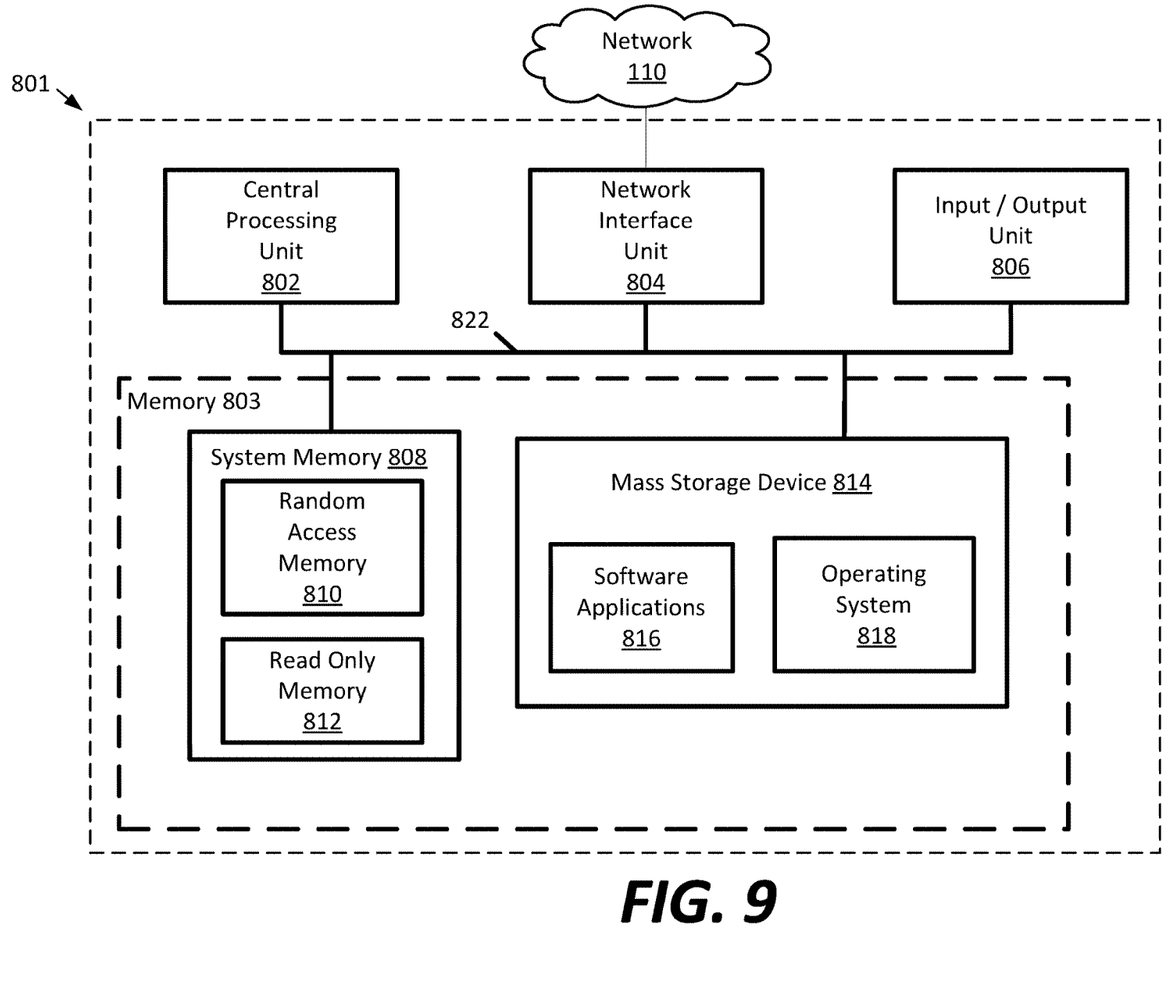
FIG. 9 shows example physical components of a computing device used in one or more devices the patient care environment of FIG. 1.

FIG. 9 shows an example computing device 801 hosting software applications 816 configured to perform some or all of the processes discussed and contemplated herein. Some or all components of example computing device 801 are typically used in the computing devices of patient care environment 100.

As illustrated, the example computing device 801 includes at least one central processing unit ("CPU") 802, memory 803, and a system bus 822 that couples the system memory 808 to the CPU 802. Memory 803 includes system memory 808 and mass storage device 814. The system memory 808 includes a random access memory ("RAM") 810 and a read-only memory ("ROM") 812. A basic input/output system that contains the basic routines that help to transfer information between elements within the example computing device 801, such as during startup, is stored in the ROM 812. The example computing device 801 further includes a mass storage device 814. The mass storage device 814 is able to store software instructions and data.

The mass storage device 814 is connected to the CPU 802 through a mass storage controller (not shown) connected to the system bus 822. The mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments of the disclosure, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software instructions, that when executed by the CPU 802, cause the example computing device 801 to provide the functionality of the example computing device 801 discussed herein. For example, the mass storage device 814 and/or the RAM 810 can store software instructions that, when executed by the CPU 802, cause the example computing device 801 to transmit a request for a patient blob.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

The description and illustration of one or more embodiments provided in this application are not intended to limit or restrict the scope of the invention as claimed in any way. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A method for creating an authenticated connection between a monitoring device and a wireless vital sign device, the method comprising:
    provisioning at least one wireless vital sign device with an encrypted patient blob;
    transmitting a patient blob request to the at least one wireless vital sign device;
    receiving a patient blob communication from the at least one wireless vital sign device, the patient blob communication including the encrypted patient blob; and
    determining at least one patient identifier by decrypting the encrypted patient blob using a decryption key without receiving the decryption key from the at least one wireless vital sign device.

2. The method according to claim 1, further comprising:
    displaying at least one patient identifier for at least one patient;
    receiving a selection of a patient;
    transmitting a request for vital sign data to the wireless vital sign device associated with the patient; and
    receiving vital sign data from the wireless vital sign device for the patient selected.

3. The method according to claim 1, further comprising:
    enabling a discovery mode on the monitoring device; and
    after enabling the discovery mode, receiving a communication from the wireless vital sign device and making an initial connection.

4. The method according to claim 1, the encrypted patient blob including information identifying a patient or a device used to identify a specific patient, the information being used to associate vital sign data with a specific patient record.

5. The method according to claim 4, wherein the wireless vital sign device lacks decryption keys used to decrypt the encrypted patient blob, and further comprising:
    before provisioning the wireless vital sign device with the encrypted patient blob, generating the encrypted patient blob.

6. The method according to claim 1, wherein decrypting the encrypted patient blob received from the wireless vital sign device includes:
    acquiring a site key and an entity key;
    combining the site key and the entity key using one or more key-combining algorithms, thereby generating the decryption key; and
    decrypting the patient blob using the decryption key.

7. The method according to claim 6, further comprising:
    prompting a user to select a patient identifier from a list of patient identifiers; and
    upon selection of a single patient identifier, creating a communication connection to an associated vital sign device for receiving vital sign data.

8. A patient monitoring system, comprising:
    a wireless vital sign device, the wireless vital sign device including:
        a processing unit; and
        memory storing instructions that, when executed by the processing unit, cause the wireless vital sign device to:
            receive and store an encrypted patient blob;
            transmit the encrypted patient blob upon request;
            obtain vital sign data;
            transmit the vital sign data to a monitoring device; and
    the monitoring device, including:
        a monitoring device processing unit;
        monitoring device memory storing instructions that, when executed by the monitoring device processing unit, cause the monitoring device to:
            establish an initial connection to the wireless vital sign device;
            request an encrypted patient blob from the wireless vital sign device;
            receive an encrypted patient blob from the wireless vital sign device;
            receive the vital sign data from the wireless vital sign device; and
            without receiving decryption keys from an external source, determine at least one patient identifier included in the encrypted patient blob either by decrypting the encrypted patient blob or by determining a globally unique identifier included in the encrypted patient blob by obtaining the at least one patient identifier from a database.

9. The patient monitoring system of claim 8, wherein the monitoring device memory further includes instructions that, when executed by the monitoring device processing unit, cause the monitoring device to:
  display at least one patient identifier and the vital sign data; and
  receive confirmation that the patient identifier corresponds to a patient.

10. The patient monitoring system according to claim 8, wherein the monitoring device memory further includes instructions that, when executed by the monitoring device processing unit, cause the monitoring device to:
  enable a discovery mode on the monitoring device;
  after enabling the discovery mode, receive an advertisement communication from the wireless vital sign device.

11. A method for monitoring vital signs of a patient in a medical environment, the method comprising:
  provisioning a monitoring device with a site key and an entity key by obtaining the site key and the entity key, entering the site key and the entity key into the monitoring device, storing the site key and the entity key in persistent storage, and setting an expiration date for the site key;
  obtaining an identifier;
  encrypting the identifier into a patient blob;
  writing the patient blob to a vital sign device;
  establishing an initial connection to a vital sign device;
  transmitting a patient blob request to the vital sign device;
  receiving a patient blob transmission from the vital sign device;
  decrypting the patient blob using a decryption key, without receiving the decryption key from the vital sign device, wherein decrypting is used to determine the identifier;
  displaying the identifier;
  receiving a request to connect to the vital sign device;
  forming an authenticated connection with the vital sign device; and
  receiving a vital sign data packet from the vital sign device.

12. The method according to claim 11, wherein, the identifier includes patient identifying information to be used associating vital sign data with a patient record.

13. The method according to claim 12, wherein the vital sign data are stored in a persistent patient record.

14. The method according to claim 11, wherein encrypting the identifier comprises:
  acquiring the site key and the entity key from a persistent storage;
  combining the site key and one or more entity keys using one or more key combining algorithms resulting in an encryption key;
  encrypting the identifier using an encryption algorithm and the encryption key.

15. The method according to claim 11, further comprising:
  determining that the site key needs to be replaced;
  obtaining a new site key;
  entering the new site key into the patient monitoring device;
  storing the new site key in long-term storage; and
  setting a new expiration date for the new site key.

16. The method according to claim 15 further comprising:
  removing the site key from the patient monitoring device after the expiration date;
  transmitting a vital sign data request to the vital sign device, wherein the vital sign data packet includes vital sign measurement data.

17. The method according to claim 16, wherein establishing the initial connection includes determining a preferred vital sign device using out-of-band communication.

18. The method according to claim 16, further comprising:
  prompting a user to select a patient identifier from a list of patient identifiers; and
  upon selection of a single patient identifier, creating a communication connection to an associated vital sign device for receiving vital sign data.

19. The method according to claim 11, further comprising:
  receiving a request to transfer a patient and an associated vital sign device;
  encrypting the patient blob using a public key of a new department, thereby generating an encrypted patient blob;
  providing the encrypted patient blob to the new department;
  by the new department, decrypting the encrypted patient blob using a private key;
  encrypting the patient blob using the site key and the entity key of the new department; and
  after moving the patient and the associated vital sign device to the new department, provisioning the vital sign device with the encrypted patient blob.

* * * * *